(12) United States Patent
Shore et al.

(10) Patent No.: US 6,245,885 B1
(45) Date of Patent: Jun. 12, 2001

(54) BAX-MEDIATED APOPTOSIS MODULATING REAGENTS AND METHODS

(75) Inventors: Gordon C. Shore; Ing Swie Goping, both of Montreal (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/166,028

(22) Filed: Oct. 5, 1998

(51) Int. Cl.[7] .......................... A61K 38/00; A61K 38/10; A61K 38/16
(52) U.S. Cl. ........................ 530/326; 530/300; 530/324
(58) Field of Search ................................ 530/300, 324, 530/326

(56) References Cited

U.S. PATENT DOCUMENTS

| 5,691,179 | 11/1997 | Korsmeyer . |
| 5,700,638 | 12/1997 | Korsmeyer . |

OTHER PUBLICATIONS

Han et al., "The E1B 19k protein blocks apoptosis by interacting with and inhibiting the p53–inducible and death–promoting Bax protein" *Genes Dev.* 10:461–477 (1996).
Lewis et al., "Purification and biochemical properties of soluble recombinant human Bax" *Prot. Express. Purif.* 13:120–126 (1998).
Simonen et al., "The BH3 domain of Bax is sufficient for interaction of Bax with itself and with other family members and It is required for Induction of apoptosis" *Eur. J. Biochem.* 249:85–91 (1997).
Wang et al., "Mutagenesis of the BH3 domain of Bax identified residues critical for dimerization and killing" *Mol. Cell. Biol.* 18:6083–6089 (1998).
Zha et al., "Structure–function comparisons of the proapoptotic protein Bax in yeast and mammalian cells" *Mol. Cell. Biol.* 16:6498–6508 (1996).
Antonnson et al., "Inhibition of Bax channel–forming activity by Bcl–2" *Science* 277:370–372 (1997).
Apte et al., "Mapping of the human BAX gene to chromosome 19q13.3–q13.4 and isolation of a novel alternatively spliced transcript, BAX delta" *Genomics* 26:592–594 (1995).
Cheng et al., "Bax–independent inhibition of apoptosis by Bcl–$X_L$" *Nature* 379:554–556 (1996).
Gross et al., "Enforced dimerization of BAX results in its translocation, mitochondrial dysfunction and apoptosis" *EMBO J.* 17:3878–3885 (1998).
Hengartner, "Death cycle and Swiss army knives" *Nature* 391:441–442 (1998).
Hockenbery et al., "Bcl–2 is an inner mitochondrial membrance protein that blocks programmed cell death" *Nature* 348:334–336 (1990).
Hunter et al., "A peptide sequence from Bax that converts Bcl–2 into an activator of apoptosis" *J. Biol. Chem.* 271:8521–8524 (1996).

Hsu et al., "Cytosol–to–membrane redistribution of Bax and Bcl–$X_L$ during apoptosis" *Proc. Natl. Acad. Sci. USA* 94:3668–3672 (1997).
Jürgensmeier et al., "Bax directly induces release of cytochrome c from isolated mitochondria" *Proc. Natl. Acad. Sci. USA* 95:4997–5002 (1998).
Kluck et al., "The release of cytochrome c from mitochondria: a primary site for Bcl–2 regulation of apoptosis" *Science* 275:1132–1136 (1997).
Knudson et al., "Bcl–2 and Bax function independently to regulate cell death" *Nature Genet.* 16:358–363 (1997).
Krajewski et al., "Investigation of the subcellular distribution of the Bcl–2 oncoprotein: residence in the nuclear envelope, endoplasmic reticulum, and outer mitochondrial membranes" *Cancer Res.* 53:4701–4714 (1993).
Kroemer, "The proto–oncogene Bcl–2 and its role in regulating apoptosis" *Nature Med.* 3:614–620 (1997).
Li et al., "Cytochrome c and dATP–dependent formation of Apaf–1/Caspase–9 complex initiates an apoptotic protease cascade" *Cell* 91:479–489 (1997).
Li et al., "Cleavage of BID by Caspase 8 mediates the mitochondrial damage in the Fas pathway of apoptosis" *Cell* 94:491–501 (1998).
Luo et al., "Bid, a Bcl12 interacting protein, mediates cytochrome c release from mitochondria in response to activation of cell surface death receptors" *Cell* 94:481–490 (1998).
McCarthy et al., "Inhibition of Ced–3/ICE–related proteases does not prevent cell death induced by oncogenes, DNA damage, or the Bcl–2 homologue Bak" *J. Cell Biol.* 136:215–227 (1997).
Nguyen et al., "Targeting of Bcl–2 to the mitochondrial outer membrane by a COOH–terminal signal anchor sequence" *J. Biol. Chem.* 268:25265–25268 (1993).

(List continued on next page.)

*Primary Examiner*—Geetha P. Bansal
(74) *Attorney, Agent, or Firm*—Clark & Elbing LLP; Kristina Bieker-Brady

(57) ABSTRACT

The invention features substantially purified polypeptide fragments of two specific domains, namely the ART domain and the transmembrane domain, within the BAX protein which, when administered to a cell, increase or decrease apoptosis of the cell. Also disclosed are methods for identifying compounds which, when administered to a cell, increase or decrease apoptosis of the cell. These compounds are identified based on their abilities to interact with specific domains of the BAX protein, or to alter the interaction of the BAX ART domain with the BAX transmembrane domain.

In addition, the invention provides methods for diagnosing a patient having, or predisposed to develop, a disease involving altered apoptosis by identifying a mutation in a BAX-encoding gene which results in an amino acid mutation in the BAX ART domain, a BAX transmembrane domain, or that alters the interaction of the BAX ART domain with the BAX transmembrane domain.

3 Claims, 7 Drawing Sheets

OTHER PUBLICATIONS

Nguyen et al., "Role of membrane anchor domain of Bcl–2 in suppression of apoptosis caused by E1B–defective adenovirus" *J. Biol. Chem.* 269:16521–16524 (1994).

Oltvai et al., "Bcl–2 heterodimerizes in vivo with a conserved homolog, Bax, that accelerates programmed cell death" *Cell* 74:609–619 (1993).

Pan et al., "Caspase–9, Bcl–$X_{L1}$, and Apaf–1 form a ternary complex" *J. Biol. Chem.* 273:5841–5845 (1998).

Reed, "Cytochrome c: can't live with it–can't live without it" *Cell* 91:559–562 (1997).

Rossé et al., "Bcl–2 prolongs cell survival after Bax–induced release of cytochrome c" *Nature* 391:496–499 (1998).

Schlesinger et al., "Comparison of the ion channel characteristics of proapoptotic BAX and antiapoptotic BCL–2" *Proc. Natl. Acad. Sci. USA* 94:11357–11362 (1997).

Wolter et al., "Movement of Bax from the cytosol to mitochondria during apoptosis" *J. Cell Biol.* 139:1281–1292 (1997).

Xiang et al., "BAX–induced cell death may not require interleukin Iβ–converting enzyme–like proteases" *Proc. Natl. Acad. Sci. USA* 93:14559–14563 (1996).

Yang et al., "Molecular Thanatopsis: a discourse on the BCL–2 family and cell death" *Blood* 88:386–401 (1996).

Yang et al., "Prevention of apoptosis by Bcl–2: release of cytochrome c from mitochondria blocked" *Science* 275:1129–1132 (1997).

Zha et al., "Proapoptotic protein Bax heterodimerizes with Bcl–2 and homodimerizes with Bax via a novel domain (BH3) distinct from BH1 and BH2" *J. Biol. Chem.* 271:7440–7444 (1996).

Zhivotovsky et al., "Injected cytochrome c induces apoptosis" *Nature* 39:449–450 (1998).

BAX··· TWQTVTIFVAGVLTASLTIWKKMG-COOH (SEQ ID NO: 6)
         169                    192

BCL-2··· KTLLSLALVGACITLGAYLGHK-COOH (SEQ ID NO: 7)
          218                 239

SEQUENCE LISTING

<160> NUMBER OF SEQ ID NOS: 7

<210> SEQ ID NO 1
<211> LENGTH: 19
<212> TYPE: PRT
<213> ORGANISM: Artificial Sequence
<220> FEATURE:
<223> OTHER INFORMATION: Synthetic based on consensus sequence of Homo
sapiens, Mus musculus, and Rattus norvegicus
<221> NAME/KEY: VARIANT
<222> LOCATION: (6)...(10)
<223> OTHER INFORMATION: Xaa at 6 can be E or D; Xaa at 7 can be Q or H;
Xaa at 8 can be L or P; Xaa at 9 can be R or G;
Xaa at 10 can be S or G;

<400> SEQUENCE: 1

Met Asp Gly Ser Gly Xaa Xaa Xaa Xaa Xaa Gly Gly Pro Thr Ser Ser
 1               5                  10                  15

Glu Gln Ile

<210> SEQ ID NO 2
<211> LENGTH: 57
<212> TYPE: DNA
<213> ORGANISM: Homo sapiens

<400> SEQUENCE: 2
tggcagaccg tgaccatctt tgtggcggga gtgctcaccg cctcgctcac catctgg          57

<210> SEQ ID NO 3
<211> LENGTH: 20
<212> TYPE: PRT
<213> ORGANISM: Homo sapiens

<400> SEQUENCE: 3

Met Asp Gly Ser Gly Glu Gln Pro Arg Gly Gly Pro Thr Ser Ser
 1               5                  10                  15

Glu Gln Ile Met
            20

<210> SEQ ID NO 4
<211> LENGTH: 20
<212> TYPE: PRT
<213> ORGANISM: Mus musculus

<400> SEQUENCE: 4

Met Asp Gly Ser Gly Glu Gln Leu Gly Ser Gly Gly Pro Thr Ser Ser
 1               5                  10                  15

Glu Gln Ile Met
            20

<210> SEQ ID NO 5
<211> LENGTH: 20
<212> TYPE: PRT
<213> ORGANISM: Rattus norvegicus

<400> SEQUENCE: 5

Met Asp Gly Ser Gly Asp His Leu Gly Gly Gly Gly Pro Thr Ser Ser
 1               5                  10                  15

Glu Gln Ile Met
            20

```
<210> SEQ ID NO 6
<211> LENGTH: 24
<212> TYPE: PRT
<213> ORGANISM: Homo sapiens

<400> SEQUENCE: 6

Thr Trp Gln Thr Val Thr Ile Phe Val Ala Gly Val Leu Thr Ala Ser
 1               5                  10                  15

Leu Thr Ile Trp Lys Lys Met Gly
            20

<210> SEQ ID NO 7
<211> LENGTH: 22
<212> TYPE: PRT
<213> ORGANISM: Homo sapiens

<400> SEQUENCE: 7

Lys Thr Leu Leu Ser Leu Ala Leu Val Gly Ala Cys Ile Thr Leu Gly
 1               5                  10                  15

Ala Tyr Leu Gly His Lys
            20
```

BAX-MEDIATED APOPTOSIS MODULATING REAGENTS AND METHODS

BACKGROUND OF THE INVENTION

The response of metazoan cells to apoptotic death signals depends on the status of various regulatory checkpoints in the cell. Prominent among these is the BCL-2 family of proteins whose members include dominant suppressors of cell death (Ced-9, BCL-2, BCL-XL, BCL-w, A1, and MCL-1) and proapoptotic inducers of cell death (BAX, BAK, and BCL-Xs), as well as proapoptotic inhibitors of BCL-2/BCL-$X_L$ function (BAD, BID) (Yang and Korsmeyer, Blood 88:386–401, 1996). The relationship between these family members is complex and, in the case of the BCL-2 suppressor and BAX inducer, is further complicated by their apparent ability to function autonomously in regulating cell death, while at the same time influencing one another's activities via heterodimeric interactions.

BCL-2 suppressors function upstream of caspase death effectors, such as caspase-3, to inhibit cell death. This inhibition of cell death may be accomplished in several ways, including recruitment and regulation of Ced-4-like molecules and Ced-4-like adaptors that are required for activation of initiator caspases, and recruitment of kinases and phosphatases that may regulate the activity of BCL-2-associated complexes. Moreover, regulation of BCL-2 complexes may influence the formation of ion conducting pores or the channel activities of membranes in which BCL-2 resides.

While BAX may affect all of these BCL-2 mediated events via heterodimeric modulation, BAX is also capable of autonomous pore formation in lipid bilayers. The ability of elevated levels of BAX or BAK to initiate cell death in the absence of any additional signal in vivo correlates with severe intracellular membrane dysfunction that includes redistribution of mitochondrial cytochrome c to the cytosol and induced mitochondria permeability transition.

Most BCL-2 and BAX family proteins contain at their extreme COOH-terminus a single predicted transmembrane segment (TM). In the case of BCL-2, the TM functions as a signal-anchor that targets and inserts the protein in a $N_{cyto}$-$C_{in}$ orientation into the two main membrane locations for this protein, the mitochondrial outer membrane and the endoplasmic reticulum/nuclear envelope. Strikingly, however, the ability of BAX to translocate to membrane sites, including mitochondria, is regulated in certain contexts and depends upon the cell receiving a death signal.

SUMMARY OF THE INVENTION

We have discovered that BAX targeting to mitochondria can be regulated by zVAD-sensitive caspase(s), and we have mapped two regions of the BAX protein, the $NH_2$-terminal ART domain and the COOH-terminal TM, as the regions controlling the prevention of BAX targeting to the mitochondria in the absence of a death signal. Our results demonstrate a regulated mechanism by which a death signal can cause translocation of BAX to mitochondria. Based on our results, in general, the invention features methods and reagents for modulating BAX-mediated apoptosis.

Accordingly, in a first aspect, the invention features a substantially pure polypeptide fragment that includes a BAX protein lacking an ART domain. In one embodiment, the polypeptide fragment increases apoptosis of a cell when administered to the cell (e.g., a cancer cell).

In a second aspect, the invention features a substantially pure polypeptide fragment that includes a BAX ART domain. In one embodiment, the polypeptide fragment decreases apoptosis of a cell when administered to the cell (e.g., a degenerative cell).

In preferred embodiments of the first and second aspects of the invention, polypeptide fragment is administered with a pharmaceutically acceptable carrier, and the cell is in a mammal that has or is likely to develop a disease involving altered apoptosis.

In a third aspect and a fourth aspect, the invention features two methods for diagnosing a mammal for the presence of a disease involving altered apoptosis or for an increased likelihood of developing the disease. The method of the third aspect includes the steps of: (a) isolating a sample of nucleic acid from the mammal; and (b) determining whether the nucleic acid encodes a mutated BAX protein that has an alteration in the amino acid sequence of the ART domain or the amino acid sequence of the transmembrane domain, where the presence of the alteration indicates that the mammal has a disease involving altered apoptosis or that the mammal has an increased likelihood of developing the disease. The method of the fourth aspect includes the steps of: (a) isolating a cell sample from the mammal; and (b) determining whether the sample includes a mutated BAX protein that has an alteration in the amino acid sequence of the ART domain or the amino acid sequence of the transmembrane domain, where the presence of the alteration indicates that the mammal has a disease involving altered apoptosis or that the mammal has an increased likelihood of developing the disease.

In one embodiment of the third and fourth aspects of the invention, the alteration is in the amino acid sequence of the ART domain and the alteration inhibits the interaction of the ART domain with the transmembrane domain. In another embodiment, the alteration is a deletion of the ART domain. Preferably, the mammal has a disease involving increased apoptosis or the mammal has an increased likelihood of developing a disease involving increased apoptosis.

In another embodiment of the third and fourth aspects of the invention, the alteration is in the transmembrane domain and the alteration inhibits the ability of the transmembrane domain to insert into a mitochondrial membrane. In another embodiment, the mutation strengthens the interaction of the ART domain with the transmembrane domain. Preferably, the mammal has a disease involving decreased apoptosis or the mammal has an increased likelihood of developing a disease involving decreased apoptosis.

In a fifth aspect, the invention features a method for identifying a compound that is likely to increase apoptosis of a cell that includes the steps of: (a) providing a substantially pure polypeptide fragment that includes a BAX ART domain; (b) contacting the fragment with a candidate compound; and (c) determining binding of the candidate compound to the fragment, where binding of the candidate compound to the fragment indicates that the candidate compound is a compound likely to increase apoptosis of a cell (e.g., a cancer cell).

In a sixth aspect the invention features a method for identifying a compound that is likely to decrease apoptosis of a cell that includes the steps of: (a) providing a substantially pure polypeptide fragment that includes a BAX transmembrane domain; (b) contacting the fragment with a candidate compound; and (c) determining binding of the candidate compound to the fragment, where binding of the candidate compound to the fragment indicates that the candidate compound is a compound likely to decrease apoptosis of a cell (e.g., a degenerative cell).

In various preferred aspect of the fifth and sixth aspects of the invention, the polypeptide fragment is immobilized or is part of a fusion protein. In other embodiments, the candidate compound is a protein or is a chemical (e.g., an inorganic chemical).

In a seventh aspect, the invention features a method for increasing apoptosis in a cell (e.g., a cancer cell) that includes administering to the cell an apoptosis-increasing amount of a BAX polypeptide that lacks a functional ART domain. Preferably, the ART domain is deleted.

In an eighth aspect, the invention features a method for increasing apoptosis in a cell (e.g., a cancer cell) that includes administering to the cell an apoptosis-increasing amount of a compound that inhibits the interaction of the ART domain of a BAX polypeptide with the transmembrane domain of the BAX polypeptide. In one embodiment, the compound is an antibody that specifically binds to a BAX polypeptide.

In a ninth aspect, the invention features a method for increasing apoptosis in a cell (e.g., a cancer cell) that includes administering to the cell an apoptosis-increasing amount of a compound that specifically binds to the ART domain of a BAX protein, where the compound, when bound, inhibits the interaction of the ART domain with the transmembrane domain of the BAX polypeptide. In one embodiment, the compound is an antibody that specifically binds to a BAX polypeptide.

In a tenth aspect, the invention features a method for decreasing apoptosis in a cell (e.g., a degenerative cell) that includes administering to the cell an apoptosis-decreasing amount of a compound that specifically binds to the transmembrane domain of a BAX protein, where the compound, when bound, inhibits the insertion of the transmembrane domain into a mitochondrial membrane. In one embodiment, the compound is an antibody.

In an eleventh aspect, the invention features a method for decreasing apoptosis in a cell (e.g., a degenerative cell) that includes administering to the cell an apoptosis-decreasing amount of a compound that strengthens the interaction between a transmembrane domain and an ART domain of a BAX polypeptide.

In a twelfth aspect, the invention features a substantially pure polypeptide fragment that includes a BAX transmembrane domain, where the transmembrane domain localizes to the mitochondrial membrane of a cell when added to the cytoplasm of the cell. In preferred embodiments, the fragment is bound to a compound; the compound is a second polypeptide and the polypeptide fragment is linked to the second polypeptide by an amino acid bond; and the second polypeptide is a detectable marker or a toxic protein.

In a thirteenth aspect, the invention features a method for identifying a compound that interacts with a BAX ART domain that includes the steps of: (a) providing a substantially pure polypeptide fragment that includes a BAX ART domain; (b) contacting the fragment with a candidate compound; and (c) determining binding of the candidate compound to the fragment, where binding of the candidate compound to the fragment indicates that the candidate compound is a compound that interacts with a BAX ART domain. Preferably, the polypeptide fragment is part of a fusion protein or is immobilized; and the compound is a protein or polypeptide fragment thereof which may be present in a BAX-expressing cell.

By "apoptotic regulation of targeting domain" or "ART domain" is meant a domain of a BAX protein which, in the absence of a death signal, interacts with the transmembrane domain of BAX, thereby preventing the insertion of BAX into the mitochondria. Preferably, an ART domain is the N-terminal 19 amino acids of a BAX protein. More preferably, an ART domain has the following consensus sequence starting at the $NH_2$-terminus in single letter code:

MDGSG(E/D)(Q/H)(L/P)(R/G)(S/G)GGPTSSEQI (SEQ ID NO: 1).

By "increases apoptosis" is meant a treatment which, when applied to a population of cells, results in any increase in the number of cells which undergo apoptosis relative to an untreated control. Preferably, the increase is at least 25%, more preferably the increase is at least 50%, and most preferably the increase is at least one-fold.

By "decreases apoptosis" is meant a treatment which, when applied to a population of cells, results in any decrease in the number of cells which undergo apoptosis relative to an untreated control. Preferably, the decrease is at least 25%, more preferably the decrease is at least 50%, and most preferably the decrease is at least one-fold.

By "protein" or "polypeptide" is meant any chain of at least 40 contiguous amino acids, regardless of length or post-translational modification (for example, acetylation, carboxylation, glycosylation, phosphorylation, lipidation, and acylation).

By "degenerative cell" is meant a cell that is affected in a degenerative disease. For example, a neuron affected in a patient suffering from a neurodegenerative disease is a degenerative cell. A degenerative cell may be cultured in vitro, or may reside in the patient suffering from the degenerative disease.

By "fragment" is meant any chain of contiguous amino acids, regardless of post-translational modification, that is normally contained within a longer chain of contiguous amino acids in a naturally occurring protein. Included in this definition are truncated proteins (e.g., a BAX protein lacking an ART domain). Preferably, a fragment is a chain of at least 10 contiguous amino acids, more preferably at least 15 amino acids, and most preferably at least 30 amino acids. A fragment may be chemically synthesized, or may be expressed by a prokaryotic or eukaryotic cell transformed with a fragment-encoding nucleic acid. One preferred fragment of the invention includes the BAX ART domain. Another preferred fragment of the invention includes the BAX transmembrane domain.

By a "substantially pure polypeptide" is meant a polypeptide of the invention that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. A substantially pure polypeptide of the invention may be obtained, for example, by extraction from a natural source (for example, a pathogen), by chemically synthesizing the protein, or by expression of a recombinant nucleic acid encoding such a polypeptide. Accordingly, substantially pure polypeptides include those derived from eukaryotic organisms but synthesized in prokaryotes, and vice-versa. Purity can be measured by any appropriate method, for example, column chromatography, polyacrylamide gel electrophoresis, or by HPLC analysis. It will be understood that water, buffers, and other small molecules (e.g., molecules having a molecular weight of less than 1000 daltons), may be additionally present.

By "specifically binds" is meant a compound or antibody which recognizes and binds to a particular polypeptide but that does not substantially recognize and bind other molecules in a sample, e.g., a biological sample, that naturally includes protein. One preferred compound specifically binds to the ART domain of BAX. Another preferred compound specifically binds to the BAX transmembrane domain.

By "inhibits interaction of BAX ART with BAX TM" is meant a compound which inhibits the interaction of the ART domain and the TM domain of a BAX protein. Such a compound may bind the BAX ART domain, may bind the BAX TM domain, or may bind neither the BAX ART domain nor the BAX TM domain.

By "neutralizing antibody" is meant an antibody that interferes with any of the biological activities of the BAX polypeptide, particularly the ability of BAX to participate in the inhibition of apoptosis. The neutralizing antibody may reduce the ability of BAX polypeptides to participate in apoptosis by, preferably 50%, more preferably by 70%, and most preferably by 90% or more. Any standard assay of apoptosis, including those described herein, may be used to assess potentially neutralizing antibodies.

By "pharmaceutically acceptable carrier" is meant a carrier that is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

Other features and advantages of the invention will be apparent from the following description of the preferred embodiments thereof, and from the claims.

DETAILED DESCRIPTION

Figure 1:
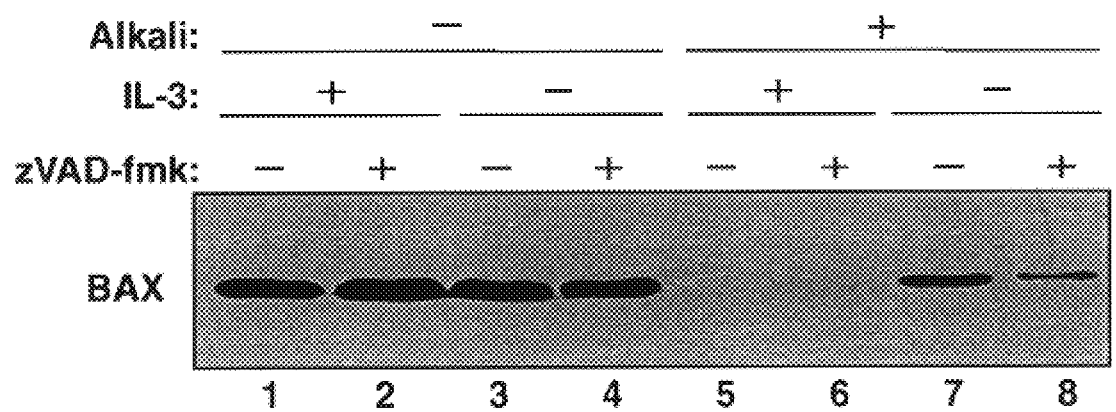
FIG. 1 is a photograph of a Western blotting analysis (immunoblotted with anti-BAX antibody) showing that mitochondrial BAX changes its alkali sensitivity following a death stimulus (withdrawal of IL-3) and that the peptidyl caspase inhibitor zVAD-fink reduces mitochondrial membrane integration of BAX.

The proapoptotic protein, BAX, contains a single predicted transmembrane domain at its COOH-terminus. In unstimulated cells, BAX is located in the cytosol and in peripheral association with intracellular membranes including mitochondria; however, following a death signal, BAX inserts into mitochondrial membrane. We have discovered that the failure of BAX to insert into mitochondrial membrane in the absence of a death signal correlated with repression of the transmembrane signal-anchor function of BAX by the $NH_2$-terminal ART (apoptotic regulation of targeting) domain. Targeting was reinstated by deleting the ART domain or by replacing the BAX transmembrane segment with that of BCL-2. In stimulated cells, the contribution of the $NH_2$-terminus of BAX correlated with further exposure of this domain following membrane insertion of the protein. The peptidyl caspase inhibitor, zVAD-fmk, partly blocked the stimulated mitochondrial membrane insertion of BAX in vivo, which was consistent with our finding of the ability of apoptotic cell extracts to support mitochondrial targeting of BAX in vitro, dependent on activation of caspase(s). Taken together, our results demonstrate that regulated targeting of BAX to mitochondria in response to a death signal is mediated by discrete domains within the BAX polypeptide.

In vivo, BAX is restrained from inserting into target membranes, including mitochondria, until the cell receives a death signal. The results described below show that BAX synthesized in a rabbit reticulocyte translation system failed to target mitochondria in vitro. Failure to target in this reconstituted mitochondrial import reaction depended on two regions within the BAX polypeptide: the $NH_2$-terminal ART domain and the COOH-terminal TM. Significantly, the TM functioned as a signal-anchor that was required for targeting and insertion into the mitochondrial outer membrane. The manifestation of this signal-anchor activity is repressed under normal conditions, and this repression depends not only on the nature of the signal-anchor itself but as well on the $NH_2$-terminal ART domain. As expected, our results demonstrate that the deletion of the ART domain enhanced the cytotoxic properties of BAX in vivo, which correlated with stimulation of membrane integration in vitro.

Following delivery of diverse death signals to cells, BAX moves to mitochondria and other membrane sites, and triggers a catastrophic transformation of mitochondrial function, including the release of cytochrome c to the surrounding cytosol, production of reactive oxygen species, loss of transmembrane potential, and induction of mitochondrial permeability transition, that result in apoptotic cell death (Xiang et al., Proc. Natl. Acad. Sci. USA. 93:14559–14563, 1996; Rosse et al., Nature 391:496–499, 1998; Reed, J. C., Cell 91:559–562, 1997; Kroemer, G, Nature Med. 3:614–620, 1997). BCL-2 proteins have the potential to intercede and block these BAX induced events at several levels.

We found that zVAD-fmk partly blocked BAX insertion into mitochondrial membrane in response to a death signal in vivo, and that an apoptotic cytosolic extract, when added in vitro to a reticulocyte lysate harboring BAX, stimulated targeting and mitochondrial membrane integration. Regulated targeting of BAX depended on both the $NH_2$-terminal ART domain and the COOH-terminal TM within the BAX molecule. These domains may mediate physical association of BAX with cytosolic or membrane proteins that control targeting, or they may be susceptible to other forms of regulation.

Fragments

Methods for generating polypeptide fragments containing various portions of the BAX protein (e.g., the ART domain or the TM domain) are well known in the art (see, for example, Ausubel et al., *Current Protocols in Molecular Biology*, John Wiley & Sons, New York, N.Y., 1994) using known nucleotide sequences. For example, a BAX ART domain-containing fragment may be generated by PCR amplifying the desired fragment using oligonucleotide primers designed based upon the BAX nucleic acid sequence (e.g., mouse BAX, GenBank Accession No. L22472; human BAX, GenBank Accession Nos. L22473 and L22474). Preferably the oligonucleotide primers include unique restriction enzyme site which facilitate insertion of the fragment into the cloning site of a prokaryotic or eukaryotic expression vector. This vector may then be used to transform a prokaryotic or eukaryotic cell (depending on which expression vector is employed), resulting in the production of the BAX ART domain-containing fragment.

Once the recombinant fragment is expressed, it may be isolated by cell lysis followed by protein purification techniques, such as affinity chromatography. For example, an anti-BAX ART domain-specific antibody, which may be produced by standard techniques (see below), may be attached to a column (e.g., a protein A sepharose column) and used to isolate the recombinant fragment. If desired, the recombinant BAX ART domain-containing fragment can be further purified, using, for example, high performance liquid chromatography (HPLC) (see, e.g., Fisher, *Laboratory Techniques In Biochemistry And Molecular Biology*, Work and Burdon, Eds., Elsevier, 1980) or other standard protein purification techniques (see, e.g., *Current Protocols in Protein Science*, ed. J. E. Coligan, John Wiley & Sons, New York, N.Y., 1996). Polypeptide fragments of the invention may also be produced by chemical synthesis (e.g., by the methods described in *Solid Phase Peptide Synthesis*, 2nd ed., 1984; The Pierce Chemical Co., Rockford, Ill.).

In one example of a use for a fragment of the invention, a BAX ART domain-containing fragment is useful for decreasing apoptosis in a cell. For example, a cell that is prone to an abnormally high amount of apoptosis (e.g., a neuron in a patient with a neurodegenerative disease) may be either introduced with BAX ART domain-containing polypeptide fragments (e.g., through liposome-mediated delivery), or may be transiently or permanently altered by gene therapy with nucleic acid encoding for the BAX ART domain-containing fragment.

In another example of a use for a fragment of the invention, a truncated BAX polypeptide lacking an ART domain (i.e., BAXΔART) is useful for increasing apoptosis in a cell. For example, a BAXΔART polypeptide fragment, or nucleic acid encoding the same) may be introduced into a cell that is prone to abnormally low amounts of apoptosis (e.g., a cancer cell).

In addition, the invention provides uses for fragments of BAX protein from a mammal (e.g., mouse, rat, human) fused to other proteins. For example, the nucleic acid molecule encoding the human BAX transmembrane domain (which has an amino acid sequence that is identical to the mouse BAX transmembrane domain shown on FIG. 4B) has the following sequence: 5' tgg cag acc gtg acc atc ttt gtg gcg gga gtg ctc acc gcc tcg ctc acc atc tgg 3' (SEQ ID NO: 2; from GenBank Accession No. L22473). (Of course, it will be understood that given the wobble of the genetic code, nucleic acid molecule having sequences other than that of SEQ ID NO: 2 may be used to encode a human or mouse BAX transmembrane domain.) With the removal of the BAX ART domain, the BAX transmembrane domain targets the resulting BAXΔART protein (as well as a DHFR-BAXTM fusion protein) to the mitochondrial membrane, even in the absence of a cell extract generated from an apoptotic cell (see FIG. 2A). Hence, fusion of the BAX transmembrane domain to any protein will result in the localization of that protein to the mitochondrial membrane. Such a specific localization may be useful, for example, in the study of mitochondrial biology where the BAX transmembrane domain is fused to a detectable marker (e.g., green fluorescent protein) which can be tracked. Mitochondrial specific localization of a protein may be used to rapidly kill a mitochondria-bearing cell (e.g., a cancer cell) by fusing the BAX transmembrane domain to a toxic protein (e.g., ricin or diptheria toxin).

Antibodies

Antibodies (e.g., polyclonal, monoclonal, single chain, humanized, chimeric) that are specific toward either a BAX ART domain or a BAX TM domain may be generated using a BAX ART domain-containing polypeptide fragment or a BAX TM-domain containing polypeptide fragment, respectively, as an antigen. Conversely, the entire BAX protein may be used as antigen, and the antibodies subsequently screened for an ability to specifically bind the ART domain or the TM domain. Standard methods for producing antibodies are well known in the art (see, e.g., Ladner, U.S. Pat. No. 4,946,778; *Current Protocols in Immunology*, ed. J. E. Coligan, John Wiley & Sons, New York, N.Y., 1991; Ward et gal., Nature 341:544–546, 1989; Green et al., Nature Genetics 7:13–21, 1994; Cabilly et al., U.S. Pat. No. 4,816,567; Boss et al., U.S. Pat. No. 4,816,397).

In one example, a BAX ART domain-specific antibody, when bound, will prevent the interaction of the ART domain with the BAX transmembrane domain, resulting in the exposure of the BAX TM domain which targets the BAX protein to the mitochondria. Such an antibody, when administered to a cell, may increase apoptosis in a BAX-containing administered cell (e.g., a cancer cell). The BAX ART-specific antibodies may directly be administered to a cell desired to undergo apoptosis, as described below, or nucleic acid encoding such antibodies may be administered.

Likewise, an antibody that specifically binds to the BAX TM domain may be used to inhibit apoptosis, even in a cell which has received a death signal (e.g., withdrawal of IL-3 from an FL5.12 cell). For example, once the death signal is received, our results have shown that the interaction between the BAX ART domain and the BAX TM domain is disrupted, thereby "freeing" the BAX TM domain, which may then target BAX to the mitochondrial membrane. However, if there is present in the cytoplasm a BAX TM domain-specific antibody, the antibody will bind to the BAX TM domain, thereby "capturing" it, and likely preventing its role in mediating the insertion of the BAX protein into the mitochrondrial membrane, thus likely preventing apoptosis.

Detection of Conditions Involving Altered Apoptosis

The invention allows for the detection or monitoring of conditions involving aberrant levels of apoptosis. For example, a disease involving an aberrant level of apoptosis (or a predisposition to develop such a disease) may be detected in a patient having a mutation in a gene encoding BAX that affects either the BAX ART domain, the BAX transmembrane (TM) domain, or both. Where the mutation results in an amino acid change that prevents the ART domain from interacting with the TM domain, the patient may have or may be predisposed to develop a disease characterized by excessive apoptosis (e.g., a degenerative disease). A mutation resulting in the truncation of the BAX polypeptide at the N-terminus may also diagnose a patient having (or predisposed to develop) a disease characterized by excessive apoptosis. Conversely, where the mutation in a BAX-encoding gene results in an amino acid change that either strengthens the interaction between the ART and TM domains and/or prevents the TM domain from inserting into the mitochondrial membrane, the patient may have (or may be predisposed to develop) a disease characterized by insufficient apoptosis (e.g., cancer).

It will be understood that the detection of an amino acid alteration the ART or transmembrane domain of a BAX protein or a BAX protein having a deletion of the ART domain may be at the nucleic acid level or at the amino acid level. For example, a nucleic acid sample may be taken from a patient and sequenced to detect a change in a nucleotide sequence that results in an amino acid sequence change. Likewise, the BAX protein may be isolated from a cell sample taken from the patient and subjected to N-terminal sequencing. Where a deletion of the ART domain is the mutation, the mutation may be readily detected by simply resolving the patient's BAX alongside normal BAX on an SDS-PAGE gel.

The methods of the instant invention may be used to treat or diagnose the disorders involving aberrant apoptosis in any mammal, for example, humans, domestic pets, or livestock. Where a non-human mammal is treated or diagnosed, the BAX protein, polypeptide fragment, nucleic acid, or antibody employed is preferably specific for that species.

Identification of Compounds that Modulate Apoptosis

The elucidation of the roles played by the ART and TM domains of BAX may be used to facilitate the identification of compounds that increase or decrease BAX-mediated apoptosis. Such compounds, when identified, may be administered to a patient suffering from a condition involving an aberrant level of apoptosis. Preferably, the compound is administered to the affected cell. Where the compound is able to traverse a cell membrane, the compound may be delivered to the general vicinity of the affected cells (e.g., injection of a compound that increases apoptosis into the center of a solid tumor). Although the following methods are used to identify a compound, these same methods may be used to ascertain either the apoptosis-inhibiting abilities of BAX ART polypeptide fragments and BAX TM-specific antibodies or the apoptosis-inducing abilities of a BAXΔART polypeptide (i.e., BAX lacking an ART domain) and a BAX ART domain specific antibody that inhibits the interaction of the ART domain with the TM domain.

In one approach, an apoptosis-enhancing compound may be identified by generating a BAX ART domain containing polypeptide fragment, according to standard techniques. Preferably, the fragment is part of a fusion protein (e.g., a GST fusion protein produced using a PGEX vector commercially available from Pharmacia Biotech, Uppsala, Sweden) that can be immobilized (e.g., on glutathione-sepharose beads). The fragment is next contacted with a candidate compound, where a compound that binds to the BAX ART domain-containing fragment is likely to increase apoptosis in an administered cell.

Where the compound that interacts with a BAX ART domain is a protein, or polypeptide fragment thereof, that interacts with the BAX ART domain in vivo, identification of such a compound allows the identification of a second compound that disrupts the interaction. Thus, administration of the second compound to a cell expressing both BAX (containing an ART domain) and the first compound may be used to increase or decrease apoptosis in that cell, depending upon the role (i.e., pro-apoptotic or apoptotic-inhibiting) of the interaction between first compound and the BAX ART domain. For example, if a first compound, when bound to the BAX ART domain, is found to inhibit apoptosis by facilitating the interaction between the BAX ART and transmembrane domains, a second compound, which disrupts the interaction of the first compound with the BAX ART domain, will likely increase apoptosis. Likewise, if a first compound, when bound to the BAX ART domain, is found to increase apoptosis (e.g., by preventing the interaction of the BAX ART and transmembrane domains, the second compound, which disrupts the interaction of the first compound with the BAX ART domain, will likely decrease apoptosis.

In a second approach, an apoptosis-enhancing compound may be identified by generating a BAX transmembrane (TM) domain containing polypeptide fragment. The fragment is next contacted with a candidate compound, where a compound that binds to the BAX TM domain-containing fragment is likely to decrease apoptosis in an administered cell.

It will be understood that in screens to identify compounds that either enhance or inhibit apoptosis, the screens are preferably high through-put screens. For example, a fragment (e.g., a myc-tagged protein fragment; Evan et al., Mol. Cell Biol. 5:3610–3616, 1985) may be immobilized to the bottom of a well on a 96 well plate. Thus, per plate, 96 different compounds may be screened. Preferably, a compound that binds the immobilized fragment may be detected using a plate reader (e.g., by fluorescence or radioactivity). For example, prior to the addition of the test compounds to the plate, the test compounds may be detectably labeled with biotin. Following addition of the test compound to the plate-bound fragments (followed by washing the plate to remove unbound compound), fluorescein-bound streptavidin may be added to the plate, which may be then read on a 96 well plate reader. Hence, a well emitting fluorescein is likely to contain a compound that binds to the plate-bound fragment.

Compounds that modulate apoptosis may be purified, or substantially urified, or may be one component of a mixture of compounds, such as an extract or supernatant obtained from cells. In an assay of a mixture of compounds, an ability to bind a BAX ART or TM domain-containing fragment is tested against progressively smaller subsets of the compound pool until a single compound or minimal number of effective compounds is demonstrated to bind.

Another method for detecting compounds that modulate apoptosis is to screen for compounds that interact with a BAX ART or BAX TM domain using a yeast two-hybrid expression system. These systems are commercially available from Clontech (Palo Alto, Calif.) and are well known (see, e.g., Gyuris et al., Cell 75:791–803, 1993; Field et al., Nature 340:245–246, 1989; and PCT Publication No. WO 95/28497). In these methods, the BAX domain (ART or TM) is used as the "bait" and the test compound will be among the library of compounds used as "prey." As above, a compound found to bind the BAX ART domain is likely to increase apoptosis in an administered cell, and a compound found to bind the BAX TM domain is likely to decrease apoptosis in an administered cell.

Test Compounds

In general, compounds that modulate apoptosis may be identified from large libraries of both natural products or synthetic (or semi-synthetic) extracts or chemical libraries according to methods known in the art. The precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Libraries of natural compounds from bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, e.g., by standard extraction and fractionation methods. If desired, any library or compound is readily modified using standard chemical, physical, or biochemical methods.

A crude extract found to modulate apoptosis may be further fractionated (according to standard fractionation and purification techniques) to isolate chemical constituents responsible for the observed effect. The same assays described herein for the detection of activities in mixtures of compounds can be used to purify the active component and to test derivatives thereof. Compounds identified as being of therapeutic value are subsequently analyzed by administration to a mammalian cell expressing BAX.

Therapies

Therapies may be designed to circumvent or overcome a BAX gene defect (e.g., a defect that affects the interaction of the BAX ART domain with the BAX TM domain), and thus restore a normal level of apoptosis to a defective cell.

a) Protein Therapy

Treatment or prevention of inappropriate apoptosis can be accomplished by eplacing mutant (e.g., point mutant or truncated) BAX protein with normal rotein delivering normal BAX protein to the appropriate cells. In addition, where a cell may or may not have mutant BAX, but exhibits an enhanced level of apoptosis (e.g., a cell affected in a degenerative disease), a BAX ART-domain containing polypeptide fragment or an antibody specific toward the BAX transmembrane domain (or both) may be administered to the cell to reduce the level of apoptosis in the administered cell. Likewise, where a cell may or may not have a mutant BAX, but exhibits an insufficient level of apoptosis (e.g., a cancer cell), a truncated BAX protein lacking an ART domain (i.e., BAXΔART) or an antibody that specifically binds to the BAX ART domain (or both) may be administered to the cell to increase the level of apoptosis in the administered cell. Delivery of the proteins, antibodies, or polypeptide fragments to the affected tissues can then be accomplished using appropriate packaging or administrating systems. Alternatively, apoptosis-modulating compounds, identified using the methods described herein, may be administered to produce the desired physiological effect.

Administration of the BAX protein, polypeptide fragment, or specific antibody may be either directly to the site of a desired apoptosis event (for example, by injection) or systemically (for example, by any conventional recombinant protein administration technique). The dosage of reagent depends on a number of factors, including the size and health of the individual patient.

b) Gene Therapy

Gene therapy is another potential therapeutic approach in which normal copies of the BAX gene are introduced into selected tissues to encode for normal protein in affected cells. The gene must be delivered to those cells in a form in which it can be taken up and encode for sufficient protein to provide effective function. Alternatively, nucleic acids encoding a truncated BAX lacking an ART domain may be administered to cells desired to undergo apoptosis (e.g., cancer cells). Likewise, nucleic acids encoding a BAX ART domain-containing polypeptide fragment may be administered to cells desired to undergo a reduced level of apoptosis (e.g., neurons in patients suffering from a neurodegenerative disease). Treatment by any gene therapy approach may be combined with more traditional therapies (e.g., surgery).

Transducing retroviral vectors may be used for somatic cell gene therapy in cells that are able to divide. Such therapy may be useful in cancer cells. Other viral vectors which can be used include adeno-associated virus, vaccinia virus, bovine papilloma virus, or a herpes virus, such as Epstein-Barr Virus, and are generally known (see, e.g., Miller, A. D., Human Gene Therapy 1:5–14, 1990; Friedman, T., Science 244:1275–1281, 1989; Eglitis and Anderson, BioTechniques 6:608–614, 1988; Tolstoshev and Anderson, Curr. Opin. Biotech. 1:55–61, 1990; Cornetta et al., Prog. Nucl. Acid Res. and Mol. Biol. 36:311–322, 1987; Anderson, W. F., Science 226:401–409, 1984; Moen, R. C., Blood Cells 17: 407–416, 1991; Miller et al., BioTechniques 7:980–990, 1989; Le Gal La Salle et al., Science 259:988–990, 1993; and Johnson, Chest 107:77S–83S, 1995). Retroviral vectors have also been developed and have been used in clinical settings (Rosenberg et al., N. Engl. J. Med 323:570–578, 1990; Anderson et al., U.S. Pat. No. 5,399,346).

Non-viral approaches may also be employed for the introduction of therapeutic nucleic acids into cells. For example, nucleic acid may be introduced into a cell by lipofection (Felgner et al., Proc. Natl. Acad. Sci. USA 84:7413–7417, 1987; Ono et al., Neurosci. Lett. 117:259–263, 1990; Brigham et al., Am. J. Med. Sci. 298:278–281, 1989; Staubinger et al., Meth. Enz. 101:512–527, 1983), asialorosonucoid-polylysine conjugation (Wu et al., J. Biol. Chem. 263:14621–14624, 1988; Wu et al., J. Biol. Chem. 264:16985–16987, 1989); or, less preferably, microinjection under surgical conditions (Wolff et al., Science 247: 1465–1468, 1990).

Gene transfer may also be achieved using non-viral means requiring transformation of cells in vitro, and then transplantation of these cells back into the body. Transformation methods include calcium phosphate, DEAE dextran, electroporation, and protoplast fusion (see, e.g., Ausubel et al., supra).

For any of the methods of application described above, the nucleic acid is preferably applied to the site of the desired apoptosis event (for example, by injection). However, it may also be applied to tissue in the vicinity of the desired apoptosis event or to a blood vessel supplying the affected cells.

In the constructs described, expression of normal BAX protein, BAX TM domain-containing fragment, or BAX ART domain-containing fragment may be directed by any suitable promoter (e.g., the human cytomegalovirus (CMV), simian virus 40 (SV40), or metallothionein promoters), and regulated by any appropriate mammalian regulatory element. Since expression of the BAXΔART protein (i.e., BAX protein lacking the ART domain) increases apoptosis in immortalized cells, it may be desirable to express that protein under the control of an inducible promoter. In addition, if desired, enhancers known to preferentially direct gene expression in a particular cell or tissue type may be used to direct expression of the BAX reagent.

Administration

A polypeptide fragment, nucleic acid, antibody, or other such compound that, using the methods of the invention, is found to modulate apoptosis, may be administered within a pharmaceutically-acceptable diluent, carrier, or excipient, in unit dosage form. Conventional pharmaceutical practice may be employed to provide suitable formulations or compositions to administer BAX ART domain-containing polypeptide fragments or antibodies specific toward the BAX transmembrane domain to patients suffering from a disease (e.g., a degenerative disease) that is caused by excessive apoptosis. Preferably, the apoptosis-inhibiting reagents are administered to the affected cell. Likewise, antibodies specific toward the BAX ART domain, or a BAX polypeptide lacking an ART domain may be administered to patients suffering from a disease (e.g., cancer) caused by insufficient apoptosis. Preferably, the apoptosis-inducing reagents are administered to the affected cell. Administration may begin before the patient is symptomatic.

Any appropriate route of administration may be employed, for example, administration may be parenteral, intravenous, intra-arterial, subcutaneous, intramuscular, intracranial, intraorbital, ophthalmic, intraventricular, intracapsular, intraspinal, intrathecal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington's Pharmaceutical Sciences* (1 $_8$t edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for the apoptosis-modulating reagents of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with an apoptosis-modulating reagent of the invention may be combined with more traditional therapies for the disease such as surgery, steroid therapy, or chemotherapy for cancer; antiviral therapy for AIDS; and tissue plasminogen activator (TPA) for ischemic injury.

There now follows a description for each of the aforementioned results. These examples are provided for the purpose of illustrating the invention, and should not be construed as limiting.

BAX Integrates into Mitochondrial Membrane Following a Death Stimulus in vivo

In the absence of a death signal during apoptosis of a cell, BAX is found free in the cytosol of the cell or is peripherally associated with endocellular membrane surfaces. We performed a Western blotting analysis of mitochondrial membranes from FL5.12 cells, immunoblotting anti-BAX antibodies (antibodies commercially available from, for example, Santa Cruz Biotech., Santa Cruz, Calif.; FIG. 1). Briefly, the mitochondrial fraction was prepared from FL5.12 cells maintained in IL-3 (FIG. 1, lanes 1, 2, 5, and 6) or deprived of IL-3 for 12 hours (FIG. 1, lanes 3, 4, 7, and 8), in the absence (FIG. 1, lanes 1, 3, 5, and 7) or presence (FIG. 1, lanes 2, 4, 6, and 8) of 50 mM zVAD-fmk for 12 hours by centrifuging at 200,000×g for 45 min. to yield supernatant and pellet fractions (the pellet fraction contains the mitochondrial membranes). The mitochondrial fractions were analyzed either directly (FIG. 1, lanes 1–4) or following extraction with 0.1 M $Na_2CO_3$, pH 11.5 (FIG. 1, lanes 5–8).

We found that in contrast to BCL-2, which is resistant to extraction at alkaline pH as a result of its integration into the membrane lipid bilayer (Nguyen et al., J. Biol. Chem. 268:25265–25268, 1993; Nguyen et al., J. Biol. Chem. 269:16521–16524, 1994), the majority of BAX was liberated under the same conditions (FIG. 1, compare lanes 1 and 5), indicative of a peripheral association with the organelle (Fujiki et al., J. Cell Biol. 93:103–110, 1982). Following induction of cell death upon withdrawal of IL-3 (Hockenbery et al., Nature 348:334–336, 1990), however, this situation was reversed and most of the BAX acquired resistance to alkaline extraction (FIG. 1, lanes 3 and 7). We concluded, therefore, that BAX demonstrates a specific response to the death signal in vivo, moving from a membrane-peripheral to a membrane-integrated position.

BAX integration into mitochondrial membrane in response to IL-3 withdrawal from FL5.12 cells for 12 hours was partly blocked by the wide spectrum caspase inhibitor, zVAD-fmk. Whereas the inhibitor did not significantly influence the recovery of total BAX associated with mitochondria (FIG. 1, compare lanes 3 and 4), it reduced the amount of alkaline-resistant, membrane-integrated BAX that was recovered with the organelle (FIG. 1, compare lanes 7 and 8). This suggests that caspases, which are activated in response to IL-3 withdrawal, stimulate mitochondrial membrane integration of BAX in vivo.

An Apoptotic Cell Extract Stimulates BAX Targeting to Mitochondria in vitro

To examine targeting of BAX into mitochondria in vitro, we employed the $^{35}$S-labelled transcription-translation product of BAX cDNA in rabbit reticulocyte lysate combined with intact mitochondria isolated from rat heart. This is a well documented system that faithfully reflects in vivo import of diverse mitochondrial proteins, including the insertion of integral proteins into the mitochondrial outer membrane (Li and Shore, Science 256:1815–1817, 1992; McBride et al., J. Cell Biol. 119:1451–1457, 1992). The various BAX constructs that were employed for these assays, and their targeting competence in vitro, are summarized in FIG. 2A.

Figure 3A:
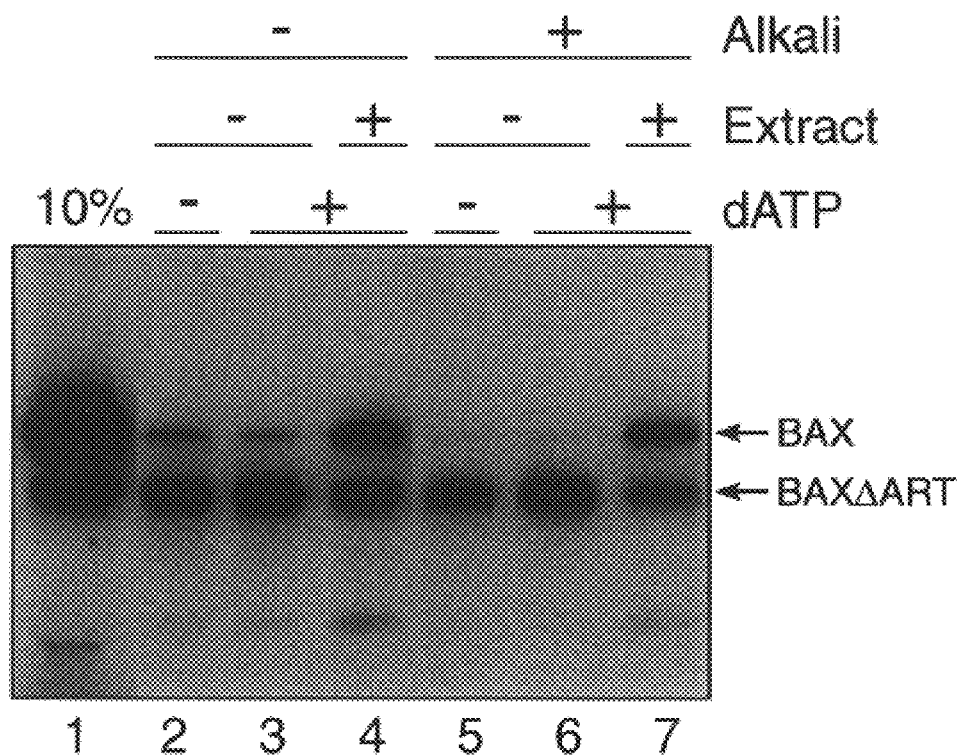
FIGS. 3A–3D are photographs (FIGS. 3A–3C) of SDS-PAGE analyses and a bar graph (FIG. 3D) showing a quantitation of such analysis demonstrating that apoptotic cell extract supports BAX targeting to mitochondria in vitro.

The results of our investigation as to whether or not apoptotic cell extract supports BAX targeting to mitochondria in vitro are presented in FIGS. 3A–3D. Briefly, in the experiments were conducted as follows. In FIG. 3A, $^{35}$S-labeled transcription-translation products of BAX cDNA in rabbit reticulocyte lysate (BAX and BAXΔART) were incubated with purified, intact mitochondria from rat heart in a standard protein import reaction supplemented with 1 mM dATP (FIG. 3A, lanes 3, 4, 6, and 7) or 1 mM dATP and 200 mg apoptotic cytosol protein (Extract) (FIG. 3A, lanes 4 and 7), in a volume of 50 ml. At the end of the reaction, mitochondria were recovered by centrifugation and the pellets analyzed by SDS PAGE and fluorography either directly or after extraction with 0.1 M $Na_2CO_3$, pH 11.5

(Alkali) (FIG. 3A, lanes 5–7). FIG. 3A, lane 1 shows 10% of input translation product.

Figure 3B:
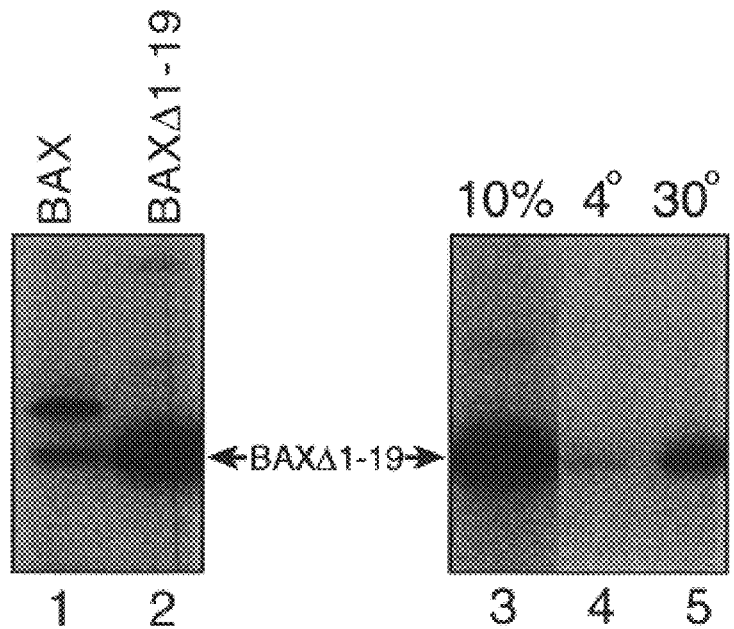

In FIG. 3B, an experiment similar to that described in FIG. 3A was performed, except that import was conducted with the BAXΔ1-19 cDNA transcription product (FIG. 3B, lane 2) at 4° C. or 30° C. as indicated, and analyzed following extraction of the mitochondria with 0.1M $Na_2CO_3$, pH 11.5 (FIG. 3B, lanes 4 and 5).

Figure 3C:
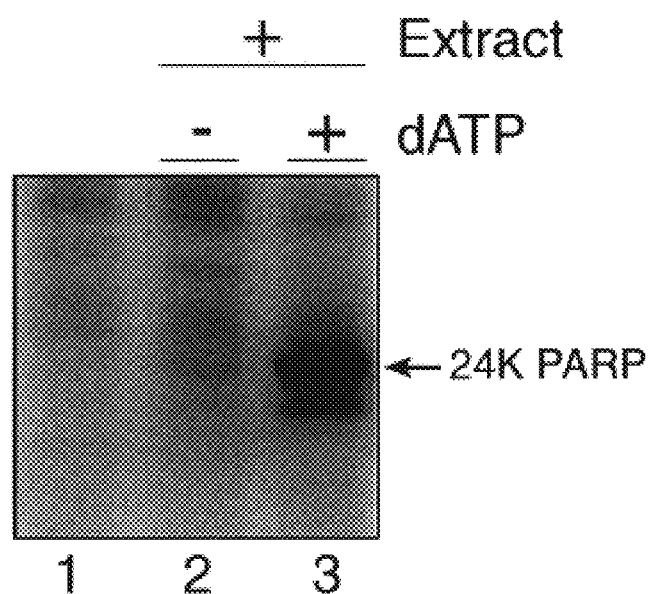

In FIG. 3C, $^{35}$S-labeled transcription-translation product of PARP cDNA in reticulocyte lysate (5% by volume) was incubated with (FIG. 3C, lanes 2 and 3) or without (FIG. 3C, lane 1) 100 mg apoptotic cytosol protein in a total volume of 20 ml, in the presence (FIG. 3C, lane 3) or absence (FIG. 3C, lanes 1 and 2) of 1 mM dATP, and equivalent portions analyzed for the appearance of the 24 kDa cleavage product of poly(ADP ribosyl) polymerase (24K PARP) by 12% SDS PAGE and fluorography.

Figure 3D:
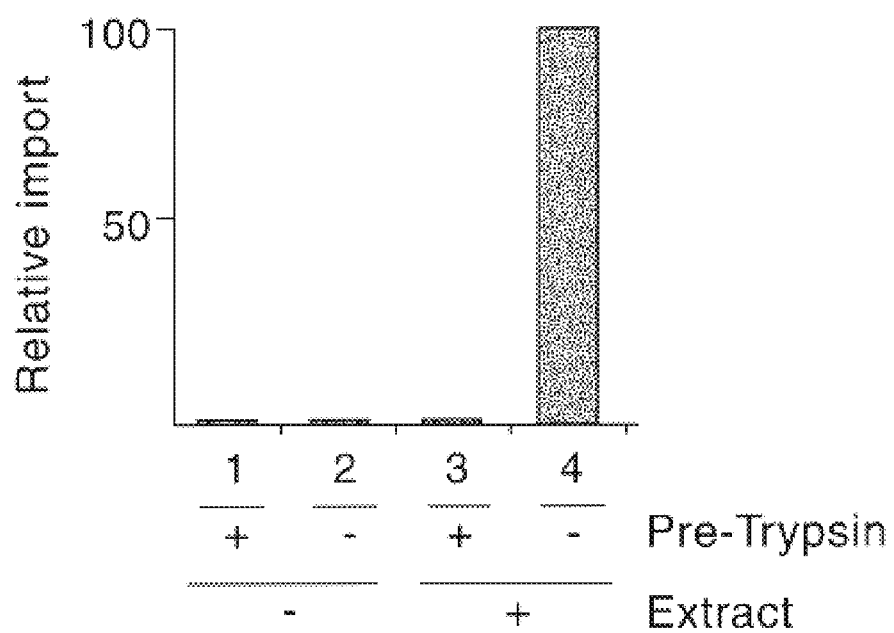

In FIG. 3D, an experiment similar to that described in FIG. 3A was performed, except that, prior to import, mitochondria were treated with 0.4 mg/ml trypsin and 50-fold weight excess soybean trypsin inhibitor added either at the beginning (−Pre-Trypsin) (FIG. 3D, columns 2 and 4) or at the end (+Pre-Trypsin) (FIG. 3D, columns 1 and 3) of the reaction. Mitochondria were collected by centrifugation and import conducted in the presence (FIG. 3D, columns 3 and 4) or absence (FIG. 3D, columns 1 and 2) of apoptotic cytosol (Extract), and the relative amount of alkali-insoluble full length BAX determined (maximum set at 100).

Transcription-translation of BAX cDNA yielded full length protein, as well as a prominent product approximately 2 kDa smaller and apparently arising from an internal translation initiation, resulting in an $NH_2$-terminal truncated BAX (designated BAXΔART). However, only the truncated BAXΔART was membrane-integrated, as judged by acquired resistance to extraction at alkaline pH (FIG. 3A, compare lanes 2 and 5).

Figures 2A, 2B:
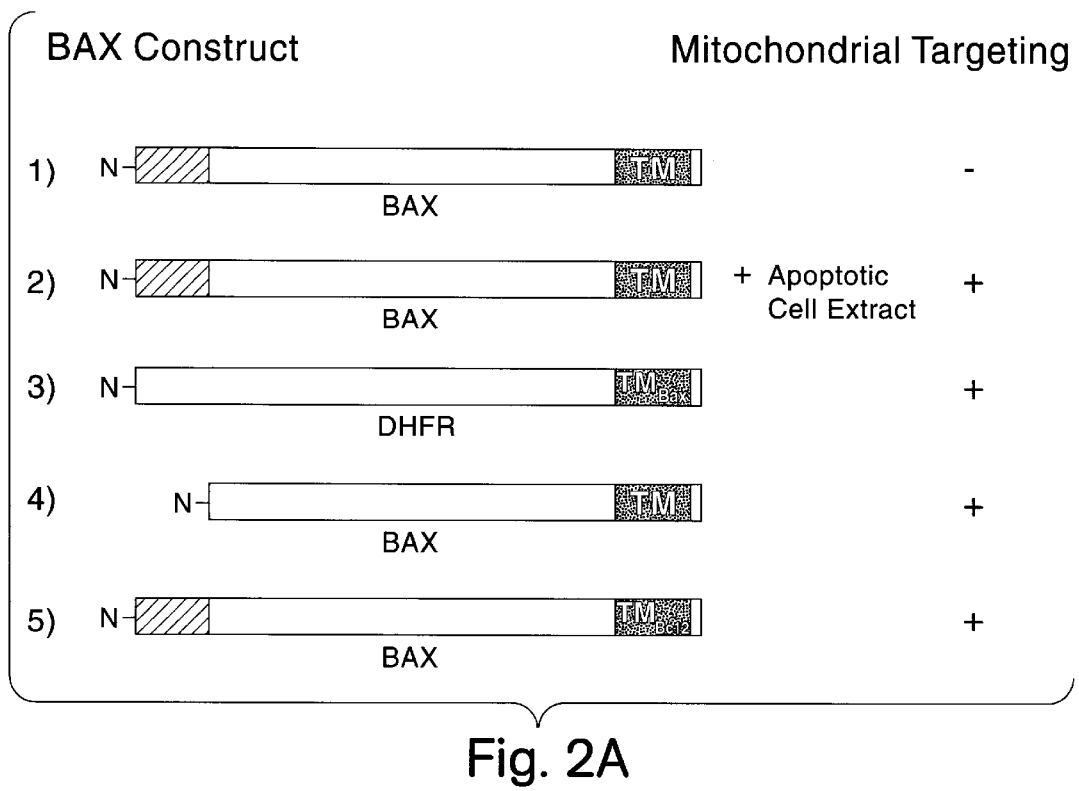
FIG. 2A is a schematic diagram showing BAX constructs and their competence for mitochondrial targeting in vitro. ART domain (hatched box); TM domain (black box); +, targeting-competent; −, targeting-incompetent. Note that where unspecified, the TM domain is from BAX.
FIG. 2B shows the sequences of amino acids 1–20 of BAX from the indicated species.

Insertion of the BAXΔART product was found to be temperature-sensitive: it occurred at 30° C. but not at 4° C. (see FIG. 4A, lanes 2–5), indicative of membrane integration rather than tight but non-specific binding (McBride et al., J. Cell Biol. 119:1451–1457, 1992). Inspection of the BAX sequence revealed the presence of an internal methionine at codon position 20 (FIG. 2B). Enforced translation initiation from met codon 20 was achieved by deleting codon 1, which yielded a product that co-migrated in SDS PAGE with BAXΔART and demonstrated temperature-sensitive membrane integration (FIG. 3B). We conclude, therefore, that amino acids 1–19 of full length BAX harbors a domain, designated ART, that is required for retention of BAX in a membrane insertion-incompetent state. This domain is rich in glycine and hydroxylated amino acid residues (FIG. 2B).

Importantly, the inability of full length BAX to target mitochondria in vitro was overcome by supplementing the import reaction mixture with an apoptotic cell extract derived from KB epithelial cells. This extract was prepared according to Liu et al. (supra) and involved cycles of freeze/thaw and homogenization of cells in hypotonic medium, causing swelling of mitochondria and consequent release of cytochrome c as a result of a ruptured outer membrane. The resulting high speed cytosolic supernatant contains endogenous procaspases whose activation can be achieved by the addition of dATP and incubation of the extract at 37° C., resulting in diagnostic cleavage of the caspase-3 death substrate, poly(ADP ribosyl) polymerase (PARP) (Liu et al., supra). The presence of this extract in import reactions stimulated binding (FIG. 3A, lanes 3 and 4) and alkaline-resistant membrane insertion of full length BAX (FIG. 3A, lanes 6 and 7), but did not stimulate BAXΔART insertion (FIG. 3A, lanes 6 and 7). Membrane-integrated BAX was accessible to exogenous trypsin in these intact mitochondria, indicative of insertion into the outer membrane.

Apoptotic activity of the cell extract was verified by demonstrating its capacity to generate the 24 kDa apoptotic fragment of PARP in response to dATP (Liu et al., supra) (FIG. 3C). Non-apoptotic high speed cytosol did not stimulate import of BAX and did not support cleavage of PARP. Also, BAX failed to target mitoplasts (mitochondria partially or wholly stripped of outer membrane) in the absence of apoptotic extract, indicating that failure to import cannot be explained by the fact that an intact outer membrane constitutes a barrier that prevents BAX from accessing the inner membrane. Finally, pretreatment of intact mitochondria with trypsin abolished subsequent membrane insertion of full length BAX in response to apoptotic extract (FIG. 3D), indicating that insertion is dependent on protein(s) exposed on the organelle surface.

ART and TM Domains are Required for Regulated Targeting of BAX in vitro

Figures 4A, 4B:
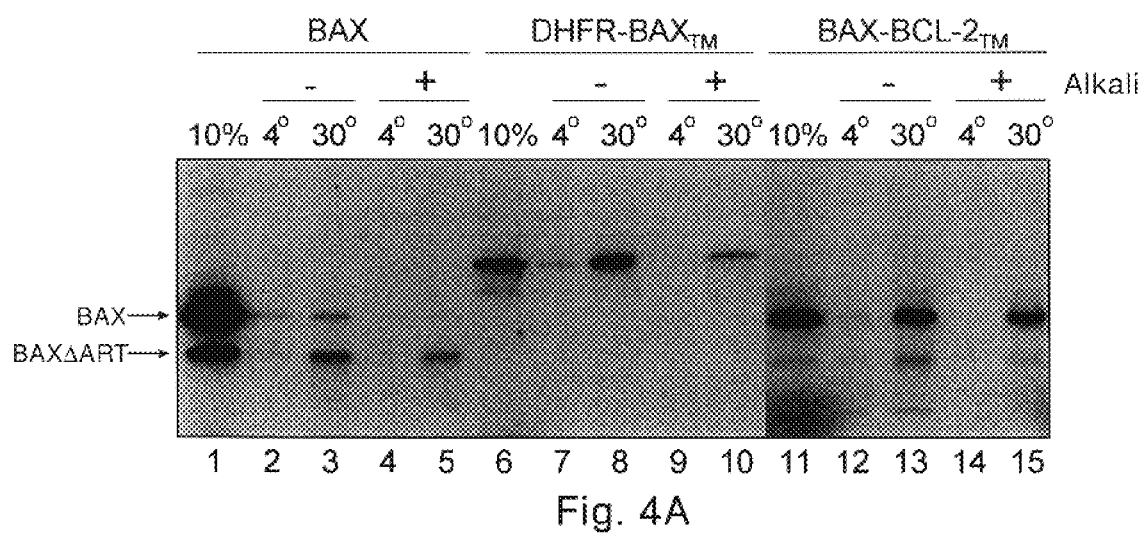
FIG. 4A is a photograph of a SDS-PAGE analysis showing that the failure of BAX to target mitochondria in vitro depends on the BAX TM domain. Lanes 1, 6, 11 represent 10% of input translation product, as indicated.
FIG. 4B shows the sequence (single letter code) of the COOH-terminal 24 amino acids of murine BAX and 22 amino acids of human BCL-2; bold letters designate the predicted transmembrane domains (TMs).

The results presented in FIGS. 3A–3D demonstrate that apoptotic regulation of BAX targeting in vitro can be by-passed by deleting the $NH_2$-terminal ART domain, resulting in constitutive targeting of the protein. We next looked at the BAX transmembrane domain, and a compared its function to that of the BCL-2 transmembrane domain (FIG. 4A). Briefly, cDNAs encoding BAX (FIG. 4A, lanes 2–5), cytosolic dihydrofolate reductase fused at its COOH-terminus to amino acids 169–192 of BAX (DHFR-BAXTM, lanes 7–10), and BAX in which the COOH-terminal 24 amino acids have been replaced by the corresponding domain of BCL-2 (amino acids 218–239) (BAX-BCL-2TM, lanes 12–15) were transcribed and translated in reticulocyte lysate and the $^{35}$S-labeled, alkali-insoluble mitochondrial import products analyzed by SDS PAGE and fluorography.

We found that replacement of the entire cytosolic portion of BAX (amino acids 1–168) with that of the monomeric reporter protein, dihydrofolate reductase (DHFR-BAXTM), permitted import into the outer membrane of intact mitochondria in the absence of apoptotic cell extract, as revealed by temperature-sensitive acquisition of resistance to extraction at alkaline pH (FIG. 4A, lanes 6–10). This result showed that the BAX TM can fuinction as a signal-anchor sequence that, in the appropriate context, is independently active in targeting and membrane insertion. It also suggested that ART, directly or indirectly, prevents manifestation of this signal-anchor function of the BAX TM in the context of the full length BAX molecule.

Importantly, however, replacement of the COOH-terminal 22 amino acids of full length BAX, which contains the TM, with the corresponding TM domain of BCL-2 now permitted targeting of the previously membrane insertion-incompetent BAX (FIG. 4A, lanes 11–15). Thus, the mechanism underlying the inability of BAX to target mitochondria in vitro requires both the presence of the specific BAX TM within the molecule, as well as the $NH_2$-terminal ART domain.

BAXΔART and BAX-BCL-2TM Exhibit Enhanced Cytotoxicity

In co-transfection experiments with a luciferase reporter as an index of survival of COS-7 and CHO cells (commercially available from the American Type Culture Collection, Rockville, Md.; Ng et al., J. Cell Biol. 139:327–338, 1997), expression of hemagglutinin epitope tagged (HA-) HA-BAXΔART or HA-BAX-BCL-2TM resulted in luciferase activity 3- to 5-times lower than that obtained with HA-BAX at 24 hours post-transfection. Moreover, when analyzed microscopically by immunofluorescence with anti-HA antibody, 7.5% of cells expressed HA-BAX at 24 hours, whereas less than 1% weakly expressed HA-BAXΔART, indicating that most cells expressing HA-BAXΔART had previously perished. Thus, the enhanced cytotoxicity of HA-BAXΔART compared to HA-BAX in vivo correlates with inhibition of BAX membrane integration by the ART domain in vitro.

Stimulation of BAX Targeting by Cell Extract Requires Cytochrome c and is Inhibited by zVAD-fmk We next performed experiments to look at the ability of apoptotic high speed cytosol to support BAX targeting to mitochondria in vitro. Briefly, in FIG. 5A, the $^{35}$S-labeled transcription-translation products of BAX cDNA were subjected to mitochondrial import in vitro in the presence of 0 (lanes 2 and 6), 13 (lanes 3 and 7), 65 (lanes 4 and 8), or 260 (lanes 5 and 9) mg apoptotic high speed cytosolic protein (Extract), with (lanes 6–9) or without (lanes 2–5) added cytochrome c (Cyt C) (75 mg/ml), and the alkali-resistant products visualized following SDS PAGE and fluorography. Lane 1 shows 10% of input translation product.

Figure 5A:
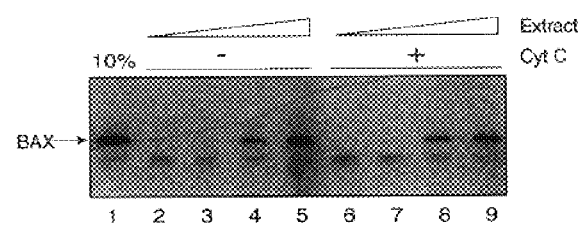
FIGS. 5A–5C are photographs of a series of SDS-PAGE analyses showing that the ability of apoptotic high speed cytosol to support BAX targeting to mitochondria in vitro depends on cytochrome c and is inhibited by zVAD-fmk.
Figure 5B:
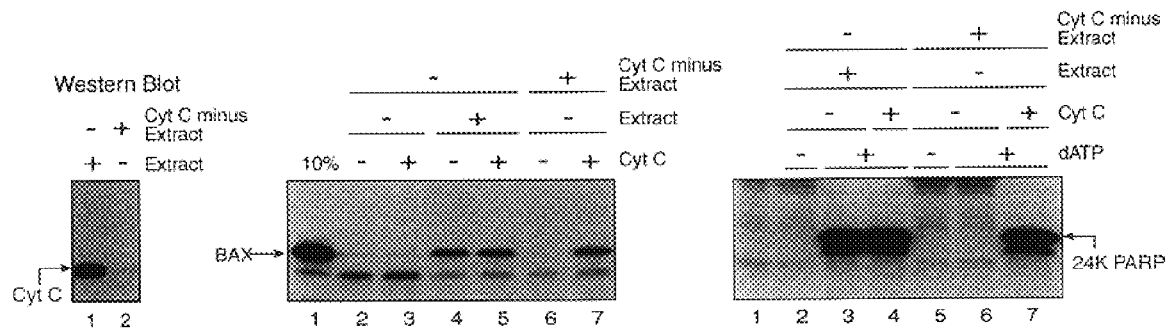

In FIG. 5B (left photograph), cytochrome c was removed from apoptotic cell extract by immunoadsorption (Cyt C minus extract), employing mouse monoclonal 2G8.B6 antibody (Mueller and Jemmerson, J. Immunol. 157:5329–5338, 1996). Equivalent aliquots of the extract before (lane 1) and after (lane 2) immunoadsorption were analyzed by Western immunoblot, employing mouse monoclonal 7H8.2C12 antibody against cytochrome c (Liu et al., Cell 86:147–157, 1996), and visualized by enhanced chemiluminescence. In FIG. 5B (middle photograph), membrane insertion of BAX translation products, determined by resistance to extraction at pH 11.5, was conducted and analyzed as in FIG. 5A, in the presence or absence of apoptotic cytosol, which had or had not been subjected to immunoadsorption with anti-cytochrome c or supplemented with added cytochrome c prior to the addition of dATP and incubation at 37° C., as indicated. In FIG. 5B (right photograph), the ability of this same apoptotic cytosol to generate the 24 kDa apoptotic cleavage product of PARP was determined under the conditions indicated, as described in FIGS. 3A–3D.

Figure 5C:
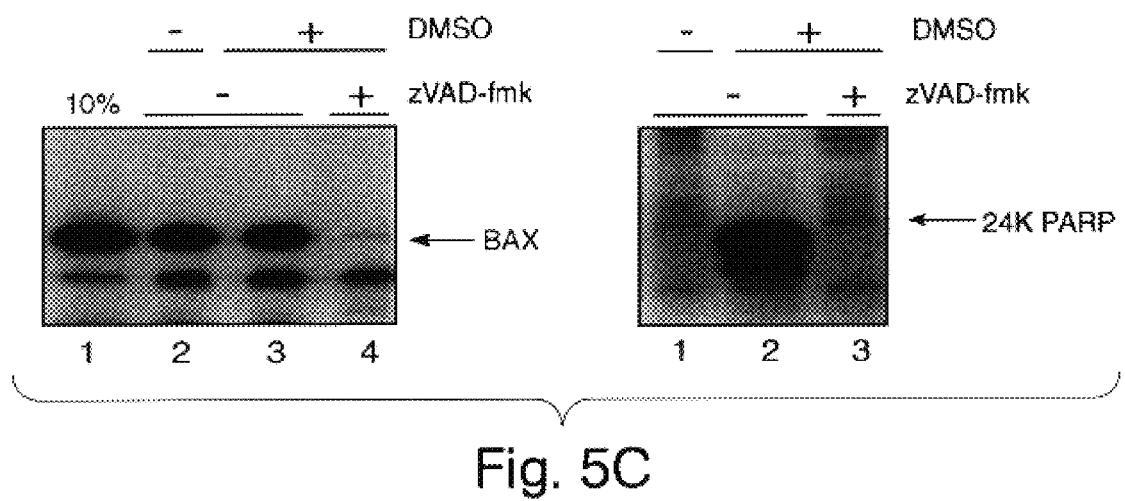

In FIG. 5C, the ability of the apoptotic high speed cytosol to support membrane insertion of BAX (alkaline-resistant product, lanes 2–4) (left photograph) and PARP cleavage (right photograph) was assayed as in FIG. 5A, in the presence or absence of 50 mM tetrapeptide zVAD-fmk which was delivered from a 100-times concentrated stock dissolved in dimethylsulfoxide prior to the addition of dATP and incubation at 37° C. An equivalent volume of this solvent had no effect on BAX import (left photograph, lane 3).

When high speed apoptotic cytosol supplemented with dATP was examined for its ability to support targeting of full length BAX to mitochondria in vitro, a marked dose-dependent stimulation was observed (FIG. 5A). No improvement to mitochondrial membrane insertion of BAX was achieved by providing additional cytochrome c (FIG. 5A lanes 6–9). The requirement for nucleotide co-factor in the apoptotic extract was not assessed because ATP, which can substitute for dATP in caspase activation, is normally required for mitochondrial protein import. Depletion of cytochrome c from the high speed cytosol by immunoadsorption prior to addition of dATP and incubation at 37° C. (FIG. 5B, left photograph), on the other hand, inhibited the ability of the extract to support BAX targeting (FIG. 5B, middle photograph, compare lanes 4 and 6) and PARP cleavage (FIG. 5B, right photograph, compare lanes 3 and 6); cytochrome c re-instated both events when added back to the extract (FIG. 5B middle and right photographs, compare lanes 6 and 7). Also, at least one other factor present in the extract was needed for cytochrome c dependent regulation of BAX targeting to mitochondria since supplementation of reticulocyte lysate translation mixtures with cytochrome c alone failed to stimulate BAX targeting. Consistent with this and with the role of cytochrome c in initiating activation of a caspase cascade (Li et al., Cell 91: 479–489, 1997), the wide spectrum inhibitor of caspases, zVAD-fmk (Zhu et al., FEBS Lett. 374:303–308, 1995), was found to effectively inhibit BAX targeting supported by apoptotic high speed cytosol (FIG. 5C left photograph, compare lanes 3 and 4) at concentrations that abolished the ability of the extract to drive PARP cleavage (FIG. 5C right photograph, compare lanes 2 and 3).

The following materials and methods were used in the above-described examples.

Plasmids

Employing standard recombinant DNA manipulations and the published sequence of murine BAX (Oltvai et al., Cell 74:609–619, 1993; GenBank Accession No. L22472), cDNA encoding murine BAXΔ1–19 (i.e., BAXΔART) was constructed in pBluescript SK, under control of the T7 promoter; the resulting translation product had an initiating methionine located 20 amino acids downstream of the original methionine of the full length BAX construct. cDNA encoding DHFR-BAXTM was created by PCR in Bluescript SK and encoded murine dihydrofolate reductase fused to the COOH-terminal 23 amino acids (residues 169–192) of BAX. Similarly, BAX-BCL-2TM was created by fusing amino acids 1–168 of BAX to amino acid 218–239 of human BCL-2. (The human BCL-2 sequence is published in Cleary et al., Cell 47:19–28, 1986; GenBank Accession No. M14745.)

Mitochondria from Rat Heart

The heart of one male Sprague Dawley rat (approximately 250 grams) was placed in approximately 100 ml HIM buffer (0.2% w/v BSA, 200 mM mannitol, 70 mM sucrose, 10 mM HEPES-KOH, 1 mM EGTA, pH 7.5) on ice, squeezed several times to force out blood, and transferred to 7.5 ml HIM in a 15-ml corex tube. All subsequent steps were conducted at 4° C. The heart was homogenized with a Polytron homogenizer (Brinkmann Instruments Inc., Westbury, N.Y.) operating for 1 second at setting 6.5. Nuclei and unbroken cells were pelleted at 1800 rpm for 10 min. in a Sorvall SS34 rotor. The supernatant was centrifuged for 10 min. at 7000 rpm. The resulting pellet was resuspended in HIM (minus BSA), centrifuged at 1800 rpm and the mitochondria were collected at 7000 rpm. The mitochondrial pellet was resuspended in cMRM (250 mM sucrose, 10 mM HEPES-KOH, 1 mM ATP, 5 mM Na Succinate, 0.08 mM ADP, 2 mM $K_2HPO_4$, pH 7.5) at a concentration of 1 mg of mitochondrial protein per ml, and adjusted to 1 mM dithiothreitol just before use.

Mitochondria from Cultured Cells

Cells were collected, washed twice with phosphate buffered saline, suspended in 2 ml HIM buffer (0.2% w/v BSA, 200 mM mannitol, 70 mM sucrose, 10 mM HEPES-KOH, 1 mM EGTA, pH 7.5), and subjected to homogenization with a Polytron homogenizer (Brinkmann Instruments Inc., Westbury, N.Y.) for 4 bursts of 10 seconds each at a setting of 6.5. All subsequent steps were conducted at 4° C. Nuclei and unbroken cells were pelleted at 1800 rpm for 10 min. in a Sorvall SS34 rotor. The supernatant was centrifuged for 10 min. at 7000 rpm. The resulting pellet was resuspended in HIM (minus BSA), centrifuged at 1800 rpm and the mitochondria were collected at 7000 rpm. The mitochondrial pellet was resuspended in cMRM (250 mM sucrose, 10 mM HEPES-KOH, 1 mM ATP, 5 mM Na Succinate, 0.08 mM ADP, 2 mM $K_2HPO_4$, pH 7.5) at a concentration of 1 mg of mitochondrial protein per ml, and adjusted to 1 mM dithiothreitol just before use.

Mitoplasts

Protein import-competent mitoplasts (mitochondria with a severely disrupted outer membrane), in which the inner membrane and transbilayer electrochemical potential remain intact, were prepared from rat liver exactly as described in McBride et al. (Biochim. Biophys. Acta. 1237:162–168, 1995).

Mitochondrial Protein Targeting in vitro cDNAs were transcribed and translated in the presence of $^{35}$S-methionine in a cell-free rabbit reticulocyte lysate system (Promega Corp., Madison, Wis.) according to the manufacturer's directions. For a standard mitochondrial protein import reaction, 5 µl of translation reaction was incubated with 20 µl of Buffer A (20 mM HEPES-KOH, 10 mM KCl, 2.5 mM $MgCl_2$, 1 mM EDTA, 1 mM EGTA, 1 mM dithiothreitol, pH 7.5) and 25 µl mitochondria or mitoplasts in cMRM (1 mg protein/ml) at 30° C. or 37° C. for 30 min. to 2 hours. The import reaction was then layered on a 500 µl cushion of 1×MRM (250 mM sucrose, 10 mM HEPES-KOH, pH 7.5) and centrifuged for 4 min. at top speed in a microfuge at 4° C. For alkali extraction, the mitochondrial pellet was resuspended (0.25 mg protein/ml) in freshly prepared 0.1 M $Na_2CO_3$, pH 11.5, and incubated for 30 min. on ice. The membranes were then pelleted in an airfuge (commercially available from Beckman Instruments Canada Inc., Montreal, PQ, Canada) operating for 10 min. at 30 psi. The pellet was analyzed by SDS-PAGE and fluorography. For import assays that included apoptotic cell extract (see below), the apoptotic cell extract replaced Buffer A (the buffer employed to make the extract, Buffer A/ext, did not influence import).

Apoptotic Cell Extract

Extract was prepared at 4° C. according to the procedure of Liu et al. (supra) with some minor modifications. Briefly, human KB epithelial cells were harvested in PBS containing 1.3 mM Na citrate and 0.6 mM EDTA. The cell pellet was washed in Buffer A/ext (50 mM PIPES, 50 mM KCl, 5 mM EGTA, 2 mM $MgCl_2$, 1 mM dithiothreitol, 20 µM cytochalasin B, pH 7.4), then resuspended in an equal volume of Buffer A/ext. The cells were disrupted by 5 cycles of freeze-thaw interspersed by 5 strokes with a Wheaton glass homogenizer fitted with a B pestle, and centrifuged at $10^5$×g for 1 hour in a Beckman Ti75 rotor. The resulting supernatant contained 10 mg protein/ml. To deplete the supernatant of cytochrome c (Liu et al., supra), 40 µl of 2G8.B6 anti-cytochrome c antibody (7.7 mg protein/ml) was first incubated with 100 µl of a 1:1 mixture of protein A and protein G Sepharose resuspended in 200 µl of PBS for 4 hours at 4° C. For the control reaction, 40 µl of Buffer A (20 mM HEPES-KOH, 10 mM KCl, 2.5 mM $MgCl_2$, 1 mM EDTA, 1 mM EGTA, 1 mM dithiothreitol, pH 7.5) was substituted for the antibody. The beads were collected, washed with Buffer A and then incubated with 125 µl of KB cell extract for 18 hours at 4° C. The beads were recovered and the supernatant collected.

Poly(ADP Ribosyl) Polymerase (PARP) Cleavage

KB apoptotic cell extract (50–100 mg protein) was incubated with 1 mM dATP in a final volume of 20 µl of Buffer A (20 mM HEPES-KOH, 10 mM KCl, 2.5 mM $MgCl_2$, 1 mM EDTA, 1 mM EGTA, 1 mM dithiothreitol, pH 7.5) at 30° C. for 1 hour, and 1 µl of $^{35}$S-methionine-labeled PARP derived by transcription-translation in rabbit reticulocyte lysate was added. After 15 min. at 30° C., 5 µl of 5×SDS sample buffer was added and 12.5 µl aliquots of each reaction were analyzed by SDS-PAGE and fluorography.

Other Embodiments

The invention further includes analogs of any naturally-occurring BAX ART domain or BAX protein lacking an ART domain. Analogs can differ from the naturally-occurring BAX ART domain or BAX protein lacking an ART domain by amino acid sequence differences, by post-translational modifications, or by both. Analogs of the invention will generally exhibit at least 85%, more preferably 90%, and most preferably 95% or even 99% identity with all or part of a naturally-occurring BAX ART domain or BAX protein lacking an ART domain amino acid sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs include genetic variants, both natural and induced (for example, resulting from random mutagenesis by irradiation or exposure to ethanemethylsulfate or by site-specific mutagenesis as described in Sambrook, Fritsch, and Maniatis, *Molecular Cloning: A Laboratory Manual* (2d ed.), CSH Press, 1989, or Ausubel et al., *Current Protocols in Molecular Biology*, John Wiley & Sons, New York, N.Y., 1994). Also included are cyclized peptides, molecules, and analogs which contain residues other than L-amino acids, e.g., D-amino acids or non-naturally occurring or synthetic amino acids, e.g., B or Y amino acids.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A substantially pure polypeptide comprising a BAXΔART protein said polypeotde lacki an ART domain, wherein said protein bas increased apoptosis inducing activity relative to a full-length BAX protein.

2. The polypeptide of claim 1, wherein said polypeptide increases apoptosis of a cell when administered to said cell.

3. The polypeptide fragment of claim 2, wherein said cell is a cancer cell.

* * * * *

UNITED STATES PATENT AND TRADEMARK OFFICE
CERTIFICATE OF CORRECTION

PATENT NO.    : 6,245,885 B1
DATED         : June 12, 2001
INVENTOR(S)   : Gordon C. Shore and Ing. Swie Goping It is certified that error appears in the above-identified patent and that said Letters Patent is hereby corrected as shown below:

<u>Title page,</u>
Item [56], OTHER PUBLICATIONS, in the "Hockenbery et al." reference, delete "membrance" and replace with -- membrane --.

<u>Column 8,</u>
Line 25, delete "et gal." and replace with -- et al., --.

<u>Column 10,</u>
Line 36, delete "urified" and replace with -- purified --.

<u>Column 11,</u>
Line 36, delete "eplacing" and replace with -- replacing --.
Line 37, delete "rotein" and replace with -- protein --.

<u>Column 13,</u>
Line 33, delete "(1 $_8$t" and replace with -- (18$^{th}$) --.

<u>Column 16,</u>
Line 28, delete "and a compared" and replace with -- and compared --.

<u>Column 17,</u>
Line 19, delete "cytrosolic" and replace with -- cytosolic --.

<u>Column 23,</u>
Line 2, delete "polypeotde lacki" and replace with -- polypeptide lacking --.
Line 3, delete "bas" and replace with -- has --.

Signed and Sealed this

Eleventh Day of February, 2003

JAMES E. ROGAN
*Director of the United States Patent and Trademark Office*